United States Patent [19]
Kelleher

[11] Patent Number: 5,486,154
[45] Date of Patent: Jan. 23, 1996

[54] ENDOSCOPE

[76] Inventor: Brian S. Kelleher, 733 Genter St., La Jolla, Calif. 92037

[21] Appl. No.: 72,935

[22] Filed: Jun. 8, 1993

[51] Int. Cl.$^6$ ..................................... A61B 1/00
[52] U.S. Cl. ......................... 600/104; 600/129; 600/157; 600/158
[58] Field of Search ....................... 128/4, 6, 7

[56] References Cited

U.S. PATENT DOCUMENTS

| Re. 34,110 | 10/1992 | Opie et al. . | |
|---|---|---|---|
| 3,858,586 | 1/1975 | Lessen . | |
| 4,646,722 | 3/1987 | Silverstein et al. | 128/4 |
| 4,662,871 | 5/1987 | Rafelson . | |
| 4,721,097 | 1/1988 | D'Amelio . | |
| 4,741,326 | 5/1988 | Sidall et al. . | |
| 4,779,611 | 10/1988 | Grooters et al. . | |
| 4,809,679 | 3/1989 | Shimonaka et al. | 128/4 |
| 4,852,551 | 8/1989 | Opie et al. . | |
| 4,878,484 | 11/1989 | Miyagi . | |
| 4,895,138 | 1/1990 | Yabe . | |
| 4,919,112 | 4/1990 | Siegmund . | |
| 4,947,827 | 8/1990 | Opie et al. | 128/4 |
| 4,974,580 | 12/1990 | Anapliotis . | |
| 4,979,496 | 12/1990 | Komi . | |
| 4,991,565 | 2/1991 | Takahashi et al. . | |
| 4,991,957 | 2/1991 | Sakamoto et al. . | |
| 4,997,084 | 5/1991 | Opie et al. . | |
| 5,020,539 | 6/1991 | Yokoi et al. . | |
| 5,036,834 | 8/1991 | Sugiyama et al. . | |
| 5,051,824 | 9/1991 | Nishigaki . | |
| 5,100,420 | 3/1992 | Green et al. . | |
| 5,133,336 | 7/1992 | Savitt et al. . | |
| 5,163,935 | 11/1992 | Black et al. . | |
| 5,169,397 | 12/1992 | Sakashita et al. . | |
| 5,201,908 | 4/1993 | Jones | 128/4 |

FOREIGN PATENT DOCUMENTS

| 0230751 | 8/1987 | European Pat. Off. . | |
|---|---|---|---|
| 7042436 | 9/1971 | France . | |
| 4220701 | 2/1993 | Germany . | |
| 4312437 | 11/1992 | Japan | 128/4 |
| 5038321 | 2/1993 | Japan | 128/4 |
| 89017973 | 3/1989 | WIPO . | |

Primary Examiner—Richard J. Apley
Assistant Examiner—Beverly M. Flanagan
Attorney, Agent, or Firm—Ellsworth R. Roston; Charles H. Schwartz

[57] ABSTRACT

An endoscope for insertion into a patient's inner body cavity has a shell with lumens for (1) illuminating a lens and (2) passing light from an imaging (or objective) lens, each lens being disposed on the distal face of the shell. The shell also has a lumen, preferably off-round, for receiving a resilient disposable core. The resilient core has passageways for introducing a pressurized fluid (e.g. air or water) to selective ones of the lenses to clean the lenses. The core may also have another passageway for removing material from the patient's inner body cavity for analysis. This passageway may communicate with two (2) conduits for removing specimens from the body cavity (1) as by a vacuum or (2) as by an instrument. The second conduit may be closed except when the instrument is to be inserted into a patient's inner body cavity. The core may be drawn through the shell lumen to position the core in the lumen. A cleaning member may be attached to the core to clean the shell lumen as the core is drawn through the lumen. Alternatively, a leader applied to the core may be drawn with the core through the shell lumen and then removed from the core. Sealing members attached to the core may also be drawn through the lumen with the core to seal the core. Alternatively, members may be sealed to the core or shell after the sealing operation. A cover on a core end may alternatively be removed after the core has been drawn through the shell lumen.

41 Claims, 5 Drawing Sheets

ENDOSCOPE

This invention relates to endoscopes for inspecting inner cavities of a patient's body, particularly those associated with the gastro-intestinal tract. More particularly, the invention relates to an endoscope with a disposable core for minimizing the cost, and facilitating the ease, of examining the inner cavities of the patient's body. The endoscope of this invention is particularly advantageous in minimizing any likelihood of cross contaminating successive patients.

BACKGROUND OF THE INVENTION

The examination of the inner cavities of a patient's body for evidences of cancer, and for polyps which sometimes lead to cancer, is becoming increasingly common. Endoscopes are employed to make such examinations. One type of endoscope employs a video sensor in the distal tip section, which sensor electrically senses the image as by a charge coupled device and sends information relating to the sensed image from the charge coupled device through a set of wires to processing and display means outside the endoscope.

Another type of endoscope generally includes at least one illuminating lens on a display face of the endoscope to illuminate the portion of the inner body cavity being inspected and also includes an imaging lens for receiving the image from the illuminated portion of the inner body cavity. Optical fibers are provided in this type of endoscope for introducing light to the illuminating lens and for receiving light from the imaging lens. The endoscopes also have passageways for obtaining specimens from the inner cavities of the patient's body such as the patient's colon. These passageways provide for obtaining specimens from the patient's inner body cavity as by suction or vacuum or as by an instrument such as forceps. The passageways may be used for other purposes such as polyp snaring, cauterizing or ablation as by lasers.

There are certain inherent limitations or disadvantages in the endoscopes now in use. One inherent disadvantage or limitation is that the endoscopes tend to provide cross contamination from a first patient to a second patient when an examination is made initially of the inner body cavity of the first patient and then of the second patient. Elaborate procedures are performed on an endoscope to clean and disinfect the endoscope after each examination of a patient's inner body cavity but such elaborate procedures are not always effective, especially with respect to cleaning the inner passageways.

To overcome the problems discussed in the previous paragraph, endoscopes have been made modular. For example, the shell holding the lenses and passageways described in the previous paragraph has been made disposable. After the inner cavity such as the colon of an individual patient has been examined, the shell has been removed and discarded. The endoscope has then been cleaned and a new shell has then been disposed on the endoscope for the examination of another patient's inner body cavity.

The procedure described in the previous paragraph has been cumbersome and expensive, particularly since the illuminating and imaging lenses have been included in the disposable shell. With the efforts now being made to limit the costs of medical procedures, endoscopes with disposable shells are becoming progressively undesirable. Furthermore, it has been found necessary to disinfect the endoscope even after the shell has been removed from the endoscope due to contamination of other parts of the endoscope not protected by the shell.

SUMMARY OF THE INVENTION

This invention provides an endoscope which overcomes the above disadvantages. The invention includes a disposable core which is removably disposed in a lumen in a shell. The disposable core is removable from the shell lumen after an inspection of an individual's inner body cavity, and the shell lumen is cleaned. Another core is then disposed in the shell lumen for an inspection of the inner body cavity of a second patient. The disposable core of this invention may be provided with features for cleaning the shell lumen as the core is drawn into the shell lumen.

In one embodiment of the invention, an endoscope for insertion into a patient's inner body cavity has a resilient shell with lumens (1) for illuminating an illuminating lens and (2) for passing light from an imaging (or objective) lens, each lens being disposed on the distal face of the shell. The shell also has a lumen, preferably off-round, for receiving a resilient disposable core. The disposable core has passageways for introducing a pressurized fluid (e.g. air or water) to selective ones of the lenses to clean the lenses.

The core may also have another passageway for removing material from the patient's inner body cavity for analysis. This passageway may communicate with two (2) conduits for removing specimens from the colon (1) as by a vacuum and (2) as by an instrument. The second conduit may be closed except when the instrument is to be inserted into a patient's inner body cavity.

The core may be drawn through the shell lumen to position the core in the lumen. A cleaning member may be attached to the core to clean the shell lumen as the core is drawn through the lumen. Alternatively, a leader applied to the core may be drawn with the core through the shell lumen and then removed from the core.

Sealing members attached to the core may also be drawn through the lumen with the core to seal the core to the shell at each end so as to prevent contamination from leaking into the lumen. Alternatively, members may be sealed to the core or shell after the drawing operation. A cover on a core end may alternatively be removed after the core has been drawn through the shell lumen.

BRIEF DESCRIPTION OF THE DRAWINGS

In the drawings:

FIG. 15 is a fragmentary sectional view of another embodiment of the invention.

DETAILED DESCRIPTION OF THE INVENTION

In one embodiment of the invention shown in FIGS. 1–4, an endoscope generally indicated at 10 is provided. The endoscope 10 includes a shell 12 made from a suitable material well known in the art. For example, the shell 12 may be made from thin strips of a helically coiled metal covered by a suitable material such as rubber, and a resilient material may be provided at the inner surface of the shell. The shell has a handle 14 which is shaped to be manually grasped. At its distal end (the end invading the patient's inner body cavity), the shell 12 has a face 16.

Figure 1:
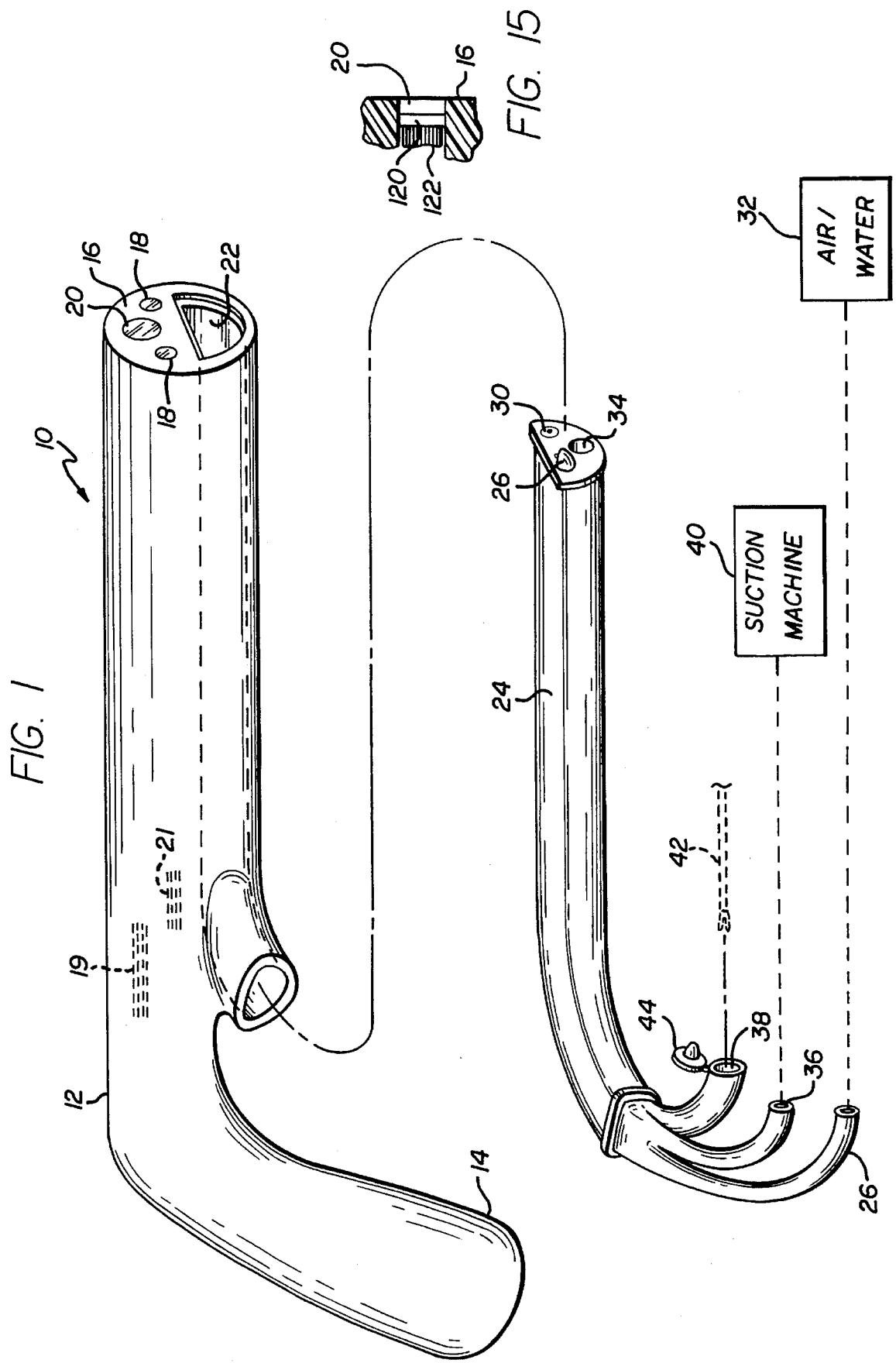
FIG. 1 is a schematic exploded perspective view of an endoscope having disposable features and constituting one embodiment of the invention.
Figure 2:
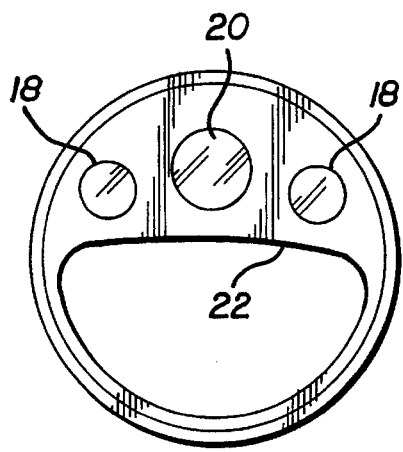
FIG. 2 is an enlarged side elevational view of certain features of a shell included in the embodiment shown in FIG. 1.
Figure 3:
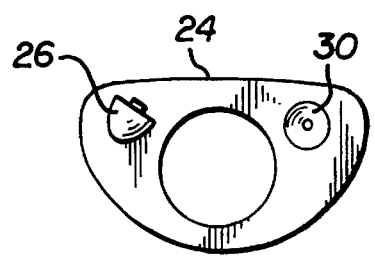
FIG. 3 is an enlarged side elevational view of certain features of a core included in the embodiment shown in FIG. 1.
Figure 4:
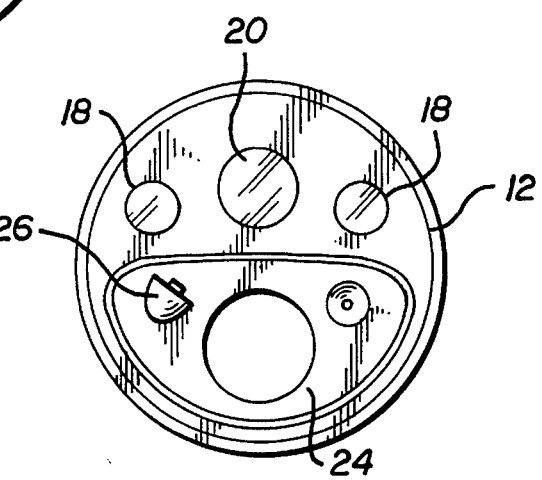
FIG. 4 is an enlarged side elevational view similar to the views shown in FIGS. 2 and 3 but with the core disposed in a lumen in the shell.

A pair of illuminating lenses 18 are disposed on the distal face 16. The illuminating lenses 18 may be constructed in a conventional manner. The illuminating lenses 18 may communicate as by optical fibers 19 through the handle 14 to an external light source in a manner well known in the art. The illuminating lenses 18 may be symmetrically disposed on the distal face 16. The illuminating lenses 18 are disposed to illuminate a portion of the patient's inner body cavity to be examined. Although two (2) illuminating lenses are shown in FIGS. 1, 2 and 4, it will be appreciated that one (1) and more than two (2) illuminating lenses may be provided on the distal face 16.

An imaging (or objective) lens 20 is also disposed on the distal face 16. The imaging lens 20 may be constructed in a conventional manner and may be preferably disposed between the illuminating lenses 18. The imaging lens 20 is constructed and disposed to provide an image of the portion of the patient's inner body cavity being examined. The imaging lens 20 may communicate as by optical fibers 21 through the handle 14 to an external viewing or display apparatus. This communication may be as by optical fibers 21 (in the case of a fiberoptic endoscope) or as by electrical wires (in the case of a video endoscope).

The shell 12 has a lumen 22 extending longitudinally through the shell. Preferably the lumen 22 has an off-round configuration in section. By providing the lumen 22 with an off-round configuration, a core 24 may be disposed tightly in the lumen in only one particular relationship. This is particularly true when the core 24 has an off-round configuration in section corresponding to the off-round configuration of the lumen 22. The core 24 may be made from a resilient material well known in the art. A lubricant may be provided on the external surface of the core 24 to facilitate the proper disposition of the core in the lumen 22 of the shell 12. Alternatively, a thin film of lubricant may be disposed on the surface defining the lumen 22 in the shell 12 to facilitate the proper disposition of the core 24 in the lumen.

A passageway 26 communicates with an external fluid pressurizing apparatus 32 at one end and with the distal face 16 of the core 24 at the other end to receive and pass the pressurized fluid from the external apparatus. This pressurized fluid may be air or water. The pressurized fluid in the passageway 26 may be introduced to the imaging lenses 18 to clean the imaging lenses.

In like manner, a passageway 30 may be disposed longitudinally in the core 24 to communicate with the external fluid pressurizing apparatus 32 at one end and with the distal face 16 at the other end. Pressurized fluid such as air or water flows through the passageway 30 to rinse tissues in the field of view or to inflate such areas with gas. It will be appreciated that the passageways 26 and 30 may actually constitute a single passageway. The pressurized fluid such as air or water may also dry the lens 20.

A passageway 34 is also disposed longitudinally in the core 24 in communication with the distal face 16. The passageway 34 may communicate with a pair of conduits 36 and 38 at the proximal end of the core (the end near the handle 14). The conduit 36 is adapted to receive a vacuum from a suction machine 40 to suction material such as specimens or debris from the inner body cavity at the position being inspected. The conduit 38 is adapted to receive an instrument such as forceps 42 in a conventional manner to snip specimens from the patient's inner body cavity at the position being inspected. A plug 44 may be attached to the wall of the conduit 38 to close the conduit when a vacuum is provided in the conduit 36. Alternatively, a rubber diaphragm with a small self-sealing hole or slit may be stretched across the opening in the conduit 38 in place of the plug 44, as is well known in the art. An instrument such as the forceps 42 or the like may be inserted through the self-sealing hole or slit, which will stretch to accommodate the diameter of the forceps.

Before the core 24 is disposed in the lumen 22, the shell 12 is cleaned with water and also preferably with a disinfectant. The disinfectant is well known in the art. The cleaning and disinfecting may be provided on the external surface of the shell 12 and also in the lumen 22. The cleaning and disinfecting are provided to insure that a second patient receiving an examination of an inner body cavity with the endoscope 10 cannot be cross contaminated by a first patient whose inner body cavity was previously examined with the endoscope. Preferably the core 24 has been previously disinfected at the time of its manufacture and has been sealed after being disinfected. If the core 24 has not previously been disinfected, it should be disinfected before insertion into the lumen 22.

FIGS. 5–10 illustrate different arrangements for sealing the core 24 in the lumen 22 of the shell 12. Although FIGS. 5–10 illustrate arrangements for sealing the core at the distal opening of the lumen, it will be appreciated that similar arrangements may be made at the proximal opening of lumen 22. Although a number of sealing arrangements are shown in FIGS. 5–10, it will be appreciated that a number of other sealing arrangements may be provided without departing from the scope of the invention. The embodiments shown in FIGS. 5–10 are accordingly illustrative only.

Figure 5A:
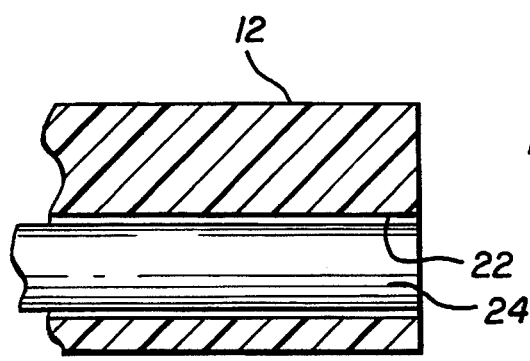
FIG. 5A is an enlarged sectional view of one embodiment including a shell and a core after the core has been disposed in the shell lumen but before the shell has been sealed to the core.
Figure 5B:
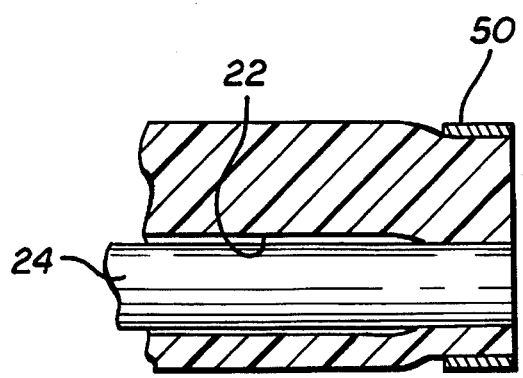
FIG. 5B is a view similar to that shown in FIG. 5A after the shell and the core shown in FIG. 5A have been sealed.

FIG. 5A illustrates the shell 12, the lumen 22 in the core 24 after the core 24 has been properly disposed in the lumen but before the shell and the core have been sealed. FIG. 5B illustrates the shell 12 and the core 24 after they have been sealed. As will be seen, the seal is provided by a ring 50 tightly disposed on the shell 12 to compress the inner end of the shell against the core 24.

Figure 6A:
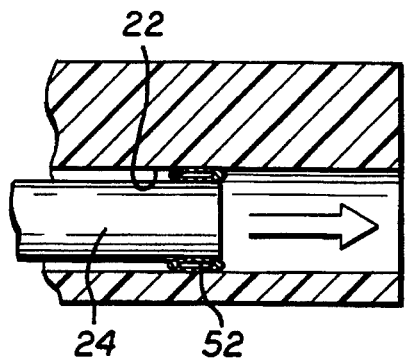
FIG. 6A is an enlarged sectional view of a second embodiment including a shell and a core after the core has been partially disposed in the core and before the shell and the core have been sealed.
Figure 6B:
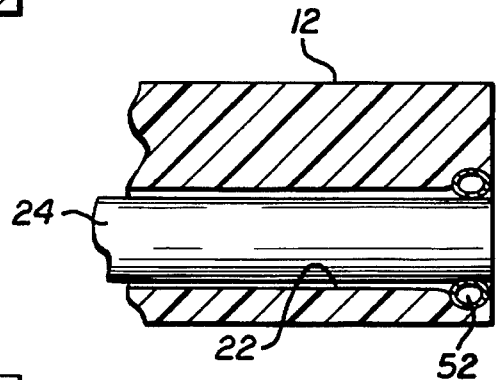
FIG. 6B is an enlarged sectional view similar to that shown in FIG. 6A after the core has been disposed in the shell and the shell and the core have been sealed.

In FIG. 6A, the core 24 has been partially inserted into the lumen 22 in the shell 12. After the core 24 has been properly inserted into the lumen 22 in the shell 12, an inflatable ring 52 on the core is inflated to expand into engagement with the wall of the lumen 22. A seal is accordingly produced between the core 24 and the lumen 22 of the shell 12 as indicated schematically in FIG. 6B. It will be appreciated that the inflatable ring 52 may be disposed on the shell 12 in the lumen 22 to expand inwardly against the core 24 when inflated.

Figure 7A:
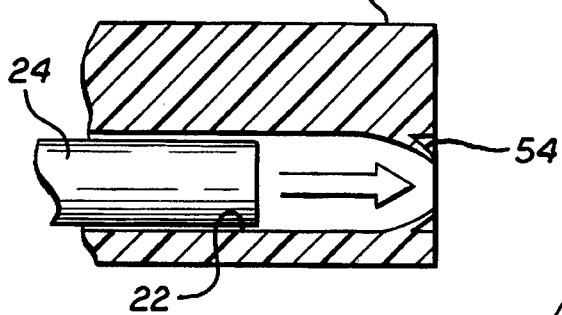
FIG. 7A is an enlarged sectional view of a third embodiment including a shell and a core after the core has been partially disposed in the shell and before the shell and the core have been sealed.
Figure 7B:
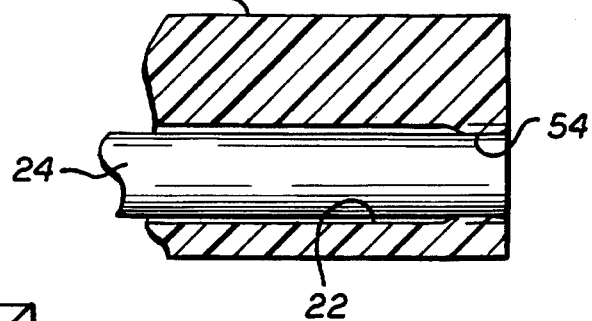
FIG. 7B is an enlarged sectional view similar to that shown in FIG. 7A after the core has been disposed in the shell and the shell and the core have been sealed.

The core 24 has also been partially inserted into the lumen 22 of the shell 12 in FIG. 7A. In this embodiment, the shell 12 is provided with a flap 54. When the shell 12 has been properly disposed in the lumen 22 of the shell 12, the flap 54 presses against the core 24 to seal the shell and the core. This is shown in FIG. 7B. As will be appreciated, the flap 56 may be formed from a cut in the internal surface of the shell as shown in FIGS. 7A and 7B or it may be formed from a flange extending longitudinally from the shell into the lumen 22 in the shell at a position past the distal end of the shell. A similar flap or flange may be formed on the external periphery of the core 24 instead of on the shell 12.

Figure 8A:
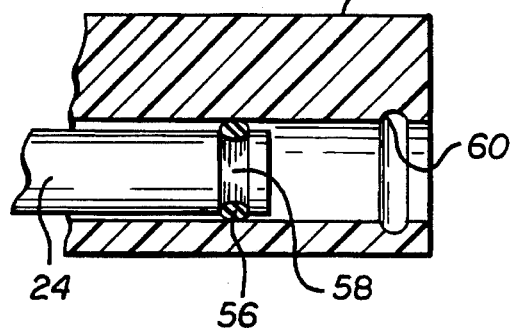
FIG. 8A is an enlarged sectional view of a fourth embodiment including a shell and a core after the core has been partially disposed in the shell and before the shell and the core have been sealed.
Figure 8B:
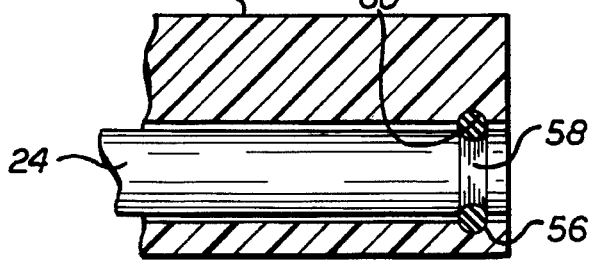
FIG. 8B is a enlarged sectional view similar to that shown in FIG. 8A after the core has been disposed in the shell and the shell and the core have been sealed.

FIGS. 8A and 8B illustrate another sealing embodiment. As shown in FIG. 8A, an O-ring 56 is seated in a socket 58 in the core 24. The core is shown in FIG. 8A after it has been partially disposed in the lumen 22 of the shell 12. The O-ring 56 becomes disposed in a socket 60 in the lumen 22 of the shell 12 after it has been fully inserted into the socket. This is shown in FIG. 8B.

A person of ordinary skill in the art will appreciate that the O-ring 56 may be seated in the shell instead of in the core. Such a person will also appreciate that the socket 60 does not have to be provided in the embodiment shown in FIGS. 8A and 8B. Alternatively, the O-ring 56 can be molded into the shell 12 or the core 24.

Figure 9A:
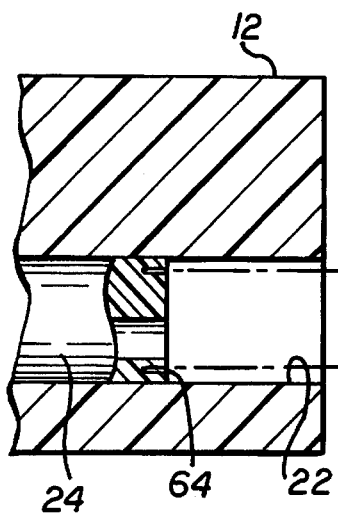
FIG. 9A is an enlarged exploded sectional view of a fifth embodiment including a shell and a core after the core has been partially disposed in the shell and before the shell and the core have been sealed.
Figure 9B:
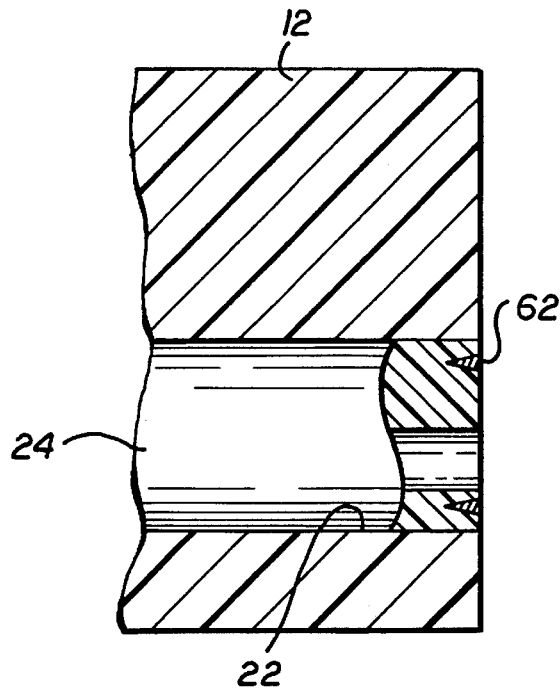
FIG. 9B is an enlarged sectional view similar to that shown in FIG. 9A after the core has been disposed in the shell and after the core and the shell have been sealed.

In FIG. 9A, the core 24 is shown as being partially disposed in the lumen 22 of the shell 12. When the core 24 has been fully disposed in the lumen 22 of the shell 12, a ring 62 is disposed in a socket 64 in the distal face of the core 24 to expand the core against the wall of the lumen 22 as shown in FIG. 9B. As will be appreciated, a ring corresponding to the ring 62 may alternatively be inserted into a socket in the shell 12 to expand the shell against the core.

Figure 10A:
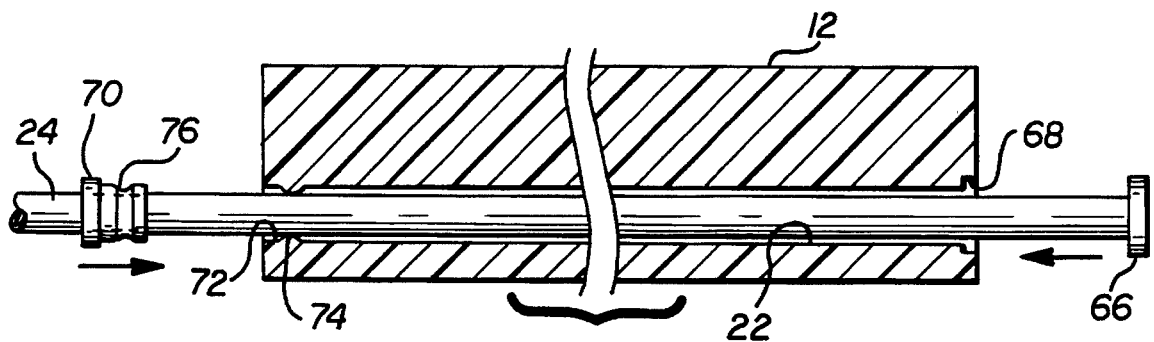
FIG. 10A is an enlarged sectional view of a sixth embodiment including a shell and a core after the core has been disposed in the shell but before the shell and the core have been sealed.
Figure 10B:
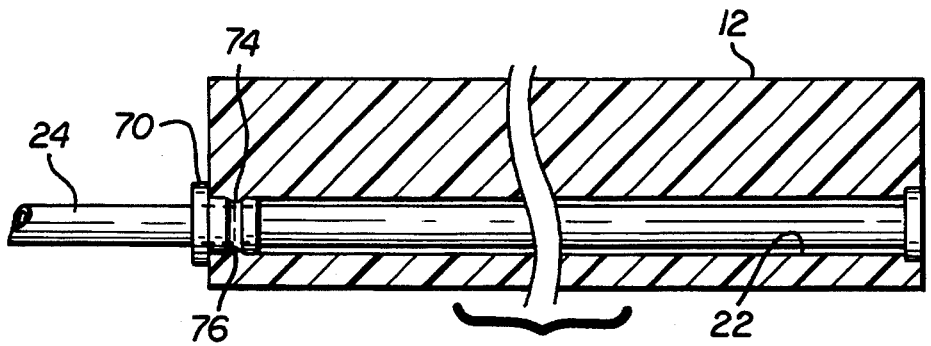
FIG. 10B is an enlarged sectional view of the shell and the core shown in FIG. 10A after the shell and the core have been sealed.

In FIG. 10A, the core 24 is shown as having been partially inserted into the lumen 22 of the shell 12. As shown in FIG. 10A, the core 24 is inserted into the shell 12 from the distal end. Upon a full insertion of the core 24 into the shell 12, a collar 66 on the core fits snugly into a socket 68 in the shell. A sleeve 70 on the core 24 is then slid on the core in a distal direction to mate with a socket 72 in the lumen 22 of the shell 12. As will be seen, a protuberance 74 on the inner wall of the shell 12 then mates with a detent portion 76 on the sleeve 70. The mating relationship is shown in FIG. 10B.

FIGS. 11–14 illustrate different arrangements for inserting the core 24 into the lumen 22 in the shell 24. A number of core configurations and insertion alternatives are shown in FIGS. 11–14.

Figure 11:
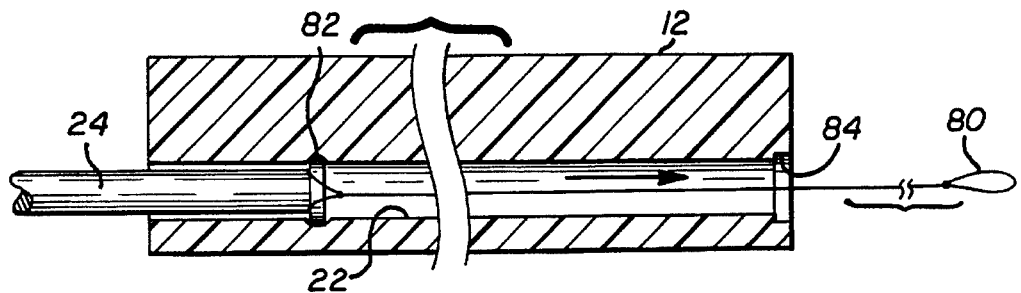
FIG. 11 is an enlarged sectional view of a shell and a core included in a seventh embodiment of the invention after the core has been partially drawn through the shell.

For example, FIG. 11 schematically shows an embodiment in which the core 24 is pulled in the distal direction as by a cord 80 through the lumen 22 in the shell 12. A collar 82 is disposed on the distal end of the core 24. When the distal end of the core 24 has been pulled to the distal end of the shell 12, the collar 82 becomes disposed in a socket 84 in the shell 12 in a tight fitting relationship.

Figure 12:
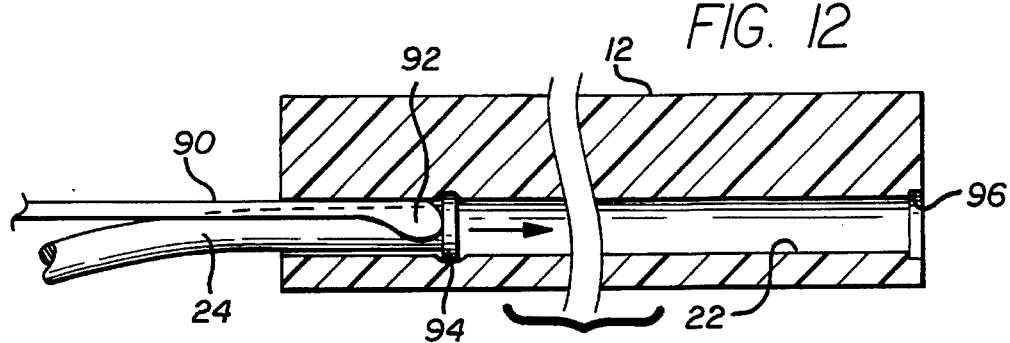
FIG. 12 is an enlarged sectional view of a shell and a core included in an eighth embodiment of the invention after the core has been partially drawn through the shell.

FIG. 12 schematically shows another arrangement for passing the core 24 through the lumen 22 in the shell 12. In the embodiment shown in FIG. 12, a rod 90 having a bulbous configuration 92 at its distal end is disposed in the lumen 22 in engagement with the core 24. When the rod 90 is moved in the distal direction, it moves the core 24 in the distal direction. When the distal end of the core 24 reaches the distal end of the shell 12, a collar 94 at the distal end of the core fits tightly in a socket 96 in the lumen 22 at the distal end of the shell. The rod 90 is then withdrawn in the proximal direction from the core 24.

Figure 13:
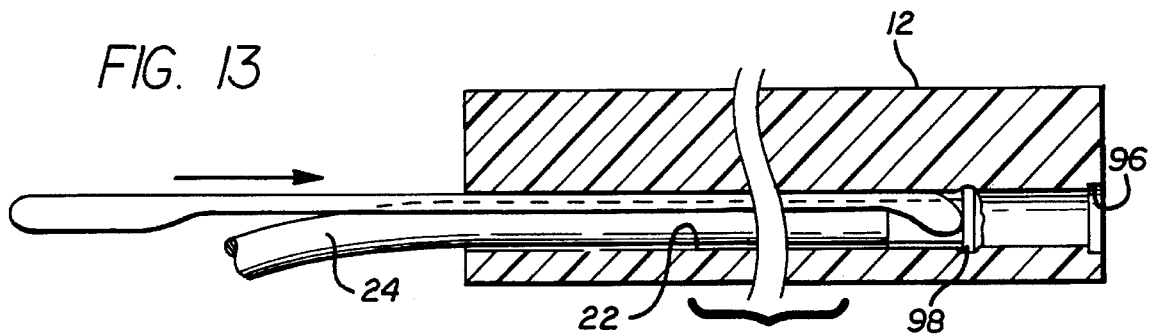
FIG. 13 is an enlarged sectional view of a shell and a core included in a ninth embodiment of the invention after the core has been partially drawn through the shell.

FIG. 13 shows an arrangement similar to that shown in FIG. 12. However, the arrangement shown in FIG. 13 includes a cover 98 for the collar 94. In this arrangement, the core 24 is moved in a distal direction through the lumen 22 in the shell 12 until the collar 94 overshoots the socket 96. This causes the collar 94 to be disposed in free space. The cover 98 is then removed from the collar 94 and the core 24 is moved in the proximal direction until the collar 94 fits tightly in the socket 96. In this way, the distal face of core 24 does not become contaminated if there should be any contaminant in the lumen 22.

Figure 14:
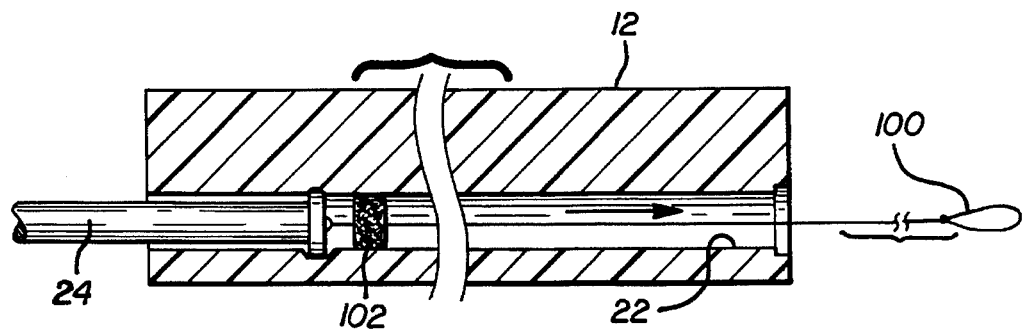
FIG. 14 is an enlarged sectional view of a shell and a core included in a tenth embodiment of the invention after the core has been partially drawn through the shell.

In FIG. 14, a cord 100 is provided corresponding to the cord 80 in FIG. 11. However, in FIG. 14, a sponge 102 is attached through the cord 100 to the core 24. The sponge 102 may be filled with a disinfectant and may be provided with a diameter slightly greater than that of the lumen 22. As the core 24 is moved in the distal direction through the lumen 22 of the shell, it engages the wall of the lumen and cleans and disinfects this wall. This provides further assurance that the endoscope is sanitary before it is applied to a patient's inner body cavity.

FIG. 15 schematically illustrates another embodiment of the invention. In this embodiment, a charge coupled device 120 (well known in the art) is disposed in back of the imaging or objective lens 20 to produce signals in accordance with the light incident on the imaging or objective lens 20. The charge coupled device 120 is connected to wires 122 which extend through the handle 16 to an external viewing or display apparatus.

The endoscope 10 constituting this invention has certain important advantages. It provides a core 24 which is disposable in a lumen 22 in a shell 12. In this way, the core 24 can be removed after use and replaced with a disinfected core. The endoscope 10 is also advantageous in that the shell 12 can be easily cleaned and disinfected after each use and after the core has been removed from the shell. The core 24 can be easily sealed in the shell 12 in a number of different ways after it has been properly inserted in the shell. The provision of a disposable core 24 is also advantageous in that it minimizes the cost of providing successive endoscopes.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. An endoscope for inspecting or applying therapy to an inner body cavity of a patient, including, a shell, illuminating means fixedly positioned in the shell, imaging means fixedly positioned in the shell, there being a lumen within the shell, and a core removably disposed within the lumen in the shell in sealing relationship with the shell with the illuminating means and the imaging means exterior in the shell to the core, the core including a first passageway disposed within the core for providing for a removal of materials from the inner body cavity of the patient.

2. An endoscope as set forth in claim 1, including, the core including a second passageway disposed within the core for applying a fluid to selected areas of the shell or inner body cavity of the patient to clean such selected areas or to inflate such cavity with gas.

3. An endoscope as set forth in claim 1, including, the core including a second passageway disposed within the core for applying a fluid to the imaging means to clean the imaging means.

4. An endoscope as set forth in claim 1, including, means disposed on at least one of the core and the shell and cooperating with the core and the shell for sealing the core within the shell.

5. An endoscope as set forth in claim 1, including, there being a lumen in the shell, the core being disposed in the lumen, and means disposed on at least one of the core and the shell and cooperating with the core and the shell for sealing the core within the lumen in the shell.

6. An endoscope for inspecting or applying therapy to an inner body cavity of a patient, including, a shell, illuminating means fixedly positioned in the shell, imaging means fixedly positioned in the shell, there being a lumen within the shell, and a core removably disposed within the lumen in the shell in sealing relationship with the shell with the illuminating means and the imaging means exterior in the shell to the core, the core including a first passageway disposed within the core for providing for a removal of materials from the inner body cavity of the patient, the lumen having a shaped configuration in section, the core being provided with a shaped configuration in section corresponding to the shaped configuration of the lumen in the shell.

7. An endoscope for inspecting or applying therapy to an inner body cavity of a patient, including, a shell made for insertion into the inner body cavity of the patient, the shell having a distal face, illuminating means fixedly disposed in the shell and extending to the distal face of the shell, imaging means fixedly disposed in the shell and extending to the distal face of the shell in spaced relationship to the illuminating means, there being a lumen in the shell, a core removably disposed within the lumen in the shell with the illuminating means and the imaging means exterior in the shell to the core, first means for sealing the core within the lumen in the shell, second means disposed within the core for cleaning at least one of the illuminating means and the imaging means in the shell, and third means disposed within the core for providing for the passage of materials between the inner body cavity of the patient and the endoscope.

8. An endoscope as set forth in claim 7, including, the second means providing for the introduction of a fluid to the imaging means to clean the imaging means, dry the imaging means or inflate the field of view in the inner body cavity of the patient.

9. An endoscope as set forth in claim 7, including, the third means including a first conduit for removing material from the inner body cavity as by suction and including a second conduit for providing for the passage of instrumentation into the inner body cavity of the patient.

10. An endoscope as set forth in claim 9, including, means for sealing the second conduit except when the instrumentation is to be inserted in the inner body cavity.

11. An endoscope as set forth in claim 10, including, means disposed within the lumen for sealing the core within the lumen in the shell.

12. An endoscope as set forth in claim 7, including, means disposed within the lumen for sealing the core within the lumen in the shell.

13. An endoscope for inspecting or applying therapy to an inner body cavity of a patient, including, a shell having a face at its distal end, illuminating means fixedly positioned in the shell and extending to the face at the distal end of the shell for illuminating a particular portion of the internal body cavity to be inspected, imaging means fixedly positioned in the shell and extending to the face at the distal end of the shell for receiving the image of the particular portion of the internal body cavity to be inspected, there being a lumen in the shell in spaced relationship to the illuminating means and the imaging means, a core removably disposed within the shell lumen with the illuminating means and the imaging means exterior in the shell to the core, first passageway means disposed within the core for introducing a fluid to at least one of the imaging means and the illuminating means through the first passageway means to clean or dry at least one of the imaging means and the illuminating means or for introducing a fluid to the particular portion of the internal body cavity through the first passageway means to clean the particular portion for inspection or to inflate the cavity with gas, and second passageway means disposed within the core in spaced relationship to the first passageway means for providing for the passage of instruments through the second passageway means or for the passage of materials through the second passageway means between the particular portion of the inner body cavity and the endoscope.

14. An endoscope as set forth in claim 13, including, the lumen having openings, means for sealing the core within the shell at the openings of the lumen and for providing for the removal of the core from the shell after the use of the shell and the core to inspect or apply therapy to the particular portion of the patient's internal body cavity.

15. In combination for use in an endoscope to inspect or apply therapy to an inner body cavity of a patient, a shell having a face at its distal end, illuminating means on the face at the distal end of the shell for illuminating a particular portion of the internal body cavity to be inspected, imaging means disposed on the face at the distal end of the shell for receiving the image of the particular portion of the internal body cavity to be inspected, there being a lumen in the shell in spaced relationship to the illuminating means and the imaging means, a core removably disposed in the shell lumen, first passageway means disposed in the core for introducing a fluid to at least one of the imaging means and the illuminating means to clean or dry such means or for introducing a fluid to the particular portion of the internal body cavity to clean the particular portion for inspection or to inflate the cavity with gas, second passageway means disposed in the core in spaced relationship to the first passageway means for providing for the passage of instruments or the passage of materials between the particular portion of the inner body cavity and the endoscope, the lumen having openings, means for sealing the core within the shell at the openings of the lumen, and means for cleaning the lumen in the shell during the insertion of the core into the aperture.

16. An endoscope as set forth in claim 10, including, the second passageway means having first and second conduit means at the proximal end, the first conduit means being constructed to become closed when a vacuum is to be applied through the second conduit means to remove materials from the patient's inner body cavity.

17. An endoscope as set forth in claim 16, including, the second conduit means being constructed to receive a vacuum to remove materials from the inner body cavity, and means for closing the first conduit means except when an instrument is inserted through the first conduit means.

18. In a combination as set forth in claim 16, means for plugging the first conduit when the second conduit receives the instrument.

19. An endoscope as set forth in claim 13, including, means disposed within the lumen for sealing the core within the lumen in the shell.

20. In combination for use in an endoscope to inspect or apply therapy to an inner body cavity of a patient where the endoscope includes a shell with a lumen having a proximal end and a distal end and a distal face and illuminating means and imaging means fixedly disposed in the shell and extending to the distal face at positions displaced from the lumen, a core made from a resilient material and shaped to fit within the lumen in the shell, the core having a first passageway within the core for receiving a fluid under pressure to clean at least one of the illuminating means and the imaging means on the distal face of the shell and having a second passageway within the core for providing for the passage of material between the inner body cavity and the endoscope, and means associated with the core and the shell for sealing the core within the shell lumen at at least one of the distal and proximal ends of the lumen.

21. In a combination as set forth in claim 20, the first passageway being adapted to pass a selective one of air and water under pressure to the distal end of the core for cleaning at least one of the illuminating means and the imaging means on the shell.

22. In a combination as set forth in claim 20, the second passageway including a first conduit for receiving a vacuum for removing material from the patient's inner body cavity by suction and including a second conduit for receiving an instrument.

23. In a combination as set forth in claim 20, means disposed on the core for separating the second passageway into a first conduit for receiving a vacuum and into a second conduit for receiving an instrument, and means associated with the second conduit for sealing the second conduit except when the instrument is inserted into the second conduit.

24. In a combination as set forth in claim 20, means disposed in co-operative relationship with the core for facilitating the insertion of the core into the lumen in the shell.

25. In a combination as set forth in claim 24 wherein the facilitating means is removable from the cooperative relationship with the core after the insertion of the core into the lumen in the shell.

26. In combination for use in an endoscope to inspect or apply therapy to an inner body cavity of a patient where the endoscope includes a shell with a lumen and a distal face and illuminating means and imaging means on the distal face, a core made from a resilient material and shaped to fit into the lumen in the shell, the core having a first passageway for receiving a fluid under pressure to clean at least one of the illuminating means and imaging means on the distal face of the shell and having a second passageway for providing for the passage of material between the inner body cavity and the endoscope, means associated with the core for sealing the core in the shell lumen, and means attached to the core for cleaning the lumen in the shell during the insertion of the core into the lumen in the shell.

27. In combination for use in an endoscope to inspect or apply therapy to an inner body cavity of a patient where the endoscope includes a shaped lumen and also includes a distal face and includes illuminating means and imaging means fixedly disposed in the shell and extending to the distal face, a core made from a resilient material and having a shaped external periphery corresponding to the shaped lumen in the shell for removable disposition within the lumen, a first passageway extending longitudinally through the core for passing a fluid under pressure to at least one of the illuminating means and the imaging means on the distal face of the shell, a second passageway extending longitudinally through the core to provide for the passage of material between the inner body cavity and the endoscope or the passage of instruments, and means supported by the core for sealing the distal end of the core within the lumen in the shell.

28. In a combination as set forth in claim 27, the sealing means including means separable from the core for sealing the distal end of the core within the lumen in the shell after the core has been disposed within the lumen.

29. In a combination as set forth in claim 27, the first passageway being disposed within the core to direct fluid under pressure to the illuminating means, and a third passageway disposed within the core to direct fluid under pressure to the imaging means.

30. In a combination as set forth in claim 27, means for facilitating the insertion of the core within the lumen in the shell.

31. In a combination as set forth in claim 27, the endoscope having a proximal end, the second passageway defining first and second conduits at a position displaced from the shell in the proximal end of the core, the first conduit receiving a vacuum and introducing the vacuum to the inner body cavity through the second passageway for removing material from the inner body cavity, the second conduit receiving an instrument and passing the instrument through the second passageway for passing material between the inner body cavity and the endoscope, and means for closing the second conduit except when the second conduit is to receive the instrument.

32. In combination for use in an endoscope to inspect or apply therapy to an inner body cavity of a patient where the endoscope includes a shaped lumen and also includes a distal face and includes illuminating means and imaging means on the distal face, a core made from a resilient material and having a shaped external periphery corresponding to the shaped lumen in the shell, a first passageway extending longitudinally through the core for passing a fluid under pressure to at least one of the illuminating means and the imaging means on the distal face of the shell, a second passageway extending longitudinally through the core to provide for the passage of material between the inner body cavity and the endoscope or the passage of instruments, and means disposed in cooperative relationship with the core and the shell for sealing the distal end of the core in the lumen in the shell, means attached to the core and movable with the core through the lumen in the shell for cleaning the lumen in the shell during the insertion of the core in the lumen in the shell.

33. A method of inspecting and applying therapy to a patient's inner body cavity and of removing material from the patient's inner body cavity, including the following steps:

providing a shell having illuminating means and imaging means fixedly disposed in the shell and extending to a distal end of the shell and having a lumen extending longitudinally through the shell, the illuminating means and the imaging means being disposed within the shell at a position external to the lumen in the shell, providing a resilient core having an external periphery configured to conform to the lumen in the shell and having at least a first passageway extending longitudinally through the core for applying a fluid under pressure to at least one of the illuminating means and the imaging means and having a second passageway extending longitudinally through the core for providing for the passage of material between the patient's inner body cavity and the endoscope, cleaning the external surface of the shell and the surface in the lumen of the shell, thereafter removably disposing the core within the lumen in the shell, and sealing the core within the lumen in the shell after the desired positioning of the core within the lumen in the shell.

34. A method as set forth in claim 33 wherein the core is drawn through the lumen in the shell and a member is then activated in a particular one of the core and the shell to seal the core within the lumen in the shell after the core has been drawn through the lumen in the shell.

35. A method as set forth in claim 33 wherein a member is disposed in co-operation with the core to facilitate the insertion of the core into the lumen in the shell.

36. A method as set forth in claim 35 wherein the facilitating member is withdrawn from the core after the core has been inserted into the lumen in the shell.

37. A method as set forth in claim 33 wherein means are disposed within the lumen in the core for sealing the core within the lumen in the shell.

38. A method of inspecting and applying therapy to a patient's inner body cavity and of removing material from the patient's inner body cavity, including the following steps:

providing a shell having illuminating means and imaging means at a distal end and having a lumen extending longitudinally through the shell, providing a resilient core having an external periphery configured to conform to the lumen in the shell and having at least a first passageway extending longitudinally through the core for applying a fluid under pressure to at least one of the illuminating means and the imaging means and having a second passageway extending longitudinally through the core for providing for the passage of material between the patient's inner body cavity and the endoscope, cleaning the external surface of the shell and the surface in the lumen of the shell, thereafter removably disposing the core in the lumen in the shell, sealing the core in the shell after the desired positioning of the core in the shell, providing a resilient cleaning member at one end of the core, and moving the core and the cleaning member through the lumen in the shell to provide a cleaning of the lumen in the shell during the insertion of the core in the lumen in the shell.

39. A method of inspecting and applying therapy to a patient's inner body cavity and of removing material from the patient's inner body cavity, including the following steps:

providing a shell having illuminating means and imaging means fixedly disposed in the shell and extending to a distal end of the shell and having a lumen extending longitudinally through the shell with the illuminating means and the imaging means exterior to the lumen, providing a resilient core having an external periphery configured to conform to the lumen in the shell and having at least a first passageway extending longitudinally through the core for applying a fluid under pressure to at least one of the illuminating means and the imaging means and having a second passageway extending longitudinally through the core for providing for the passage of material between the patient's inner body cavity and the endoscope, cleaning the external surface of the shell and the surface in the lumen of the shell, thereafter removably disposing the core in the lumen in the shell, sealing the core in the shell after the desired positioning of the core in the shell, and applying a leader to the core and then drawing the leader through the lumen in the shell with the leader applied to the core and the leader being withdrawn from the core after the leader and the core have been drawn through the lumen in the shell.

40. A method of inspecting and applying therapy to a patient's inner body cavity and of removing material from the patient's inner body cavity, including the following steps:

providing a shell having illuminating means and imaging means at a distal end and having a lumen extending longitudinally through the shell, providing a resilient core having an external periphery configured to conform to the lumen in the shell and having at least a first passageway extending longitudinally through the core for applying a fluid under pressure to at least one of the illuminating means and the imaging means and having a second passageway extending longitudinally through the core for providing for the removal of material from the patient's inner body cavity, cleaning the external surface of the shell and the surface in the lumen of the shell, thereafter disposing the core in the lumen in the shell, and sealing the core in the shell after the desired positioning of the core in the shell, applying sealing means to the distal end of the core and then drawing the core through the lumen in the shell to a position where the sealing means seal the lumen at the distal end of the shell.

41. A method of inspecting and applying therapy to a patient's inner body cavity and of removing material from the patient's inner body cavity, including the following steps:

providing a shell having illuminating means and imaging means at a distal end and having a lumen extending longitudinally through the shell, providing a resilient core having an external periphery configured to conform to the lumen in the shell and having at least a first passageway extending longitudinally through the core for applying a fluid under pressure to at least one of the illuminating means and the imaging means and having a second passageway extending longitudinally through the core for providing for the passage of material between the patient's inner body cavity and the endoscope, cleaning the external surface of the shell and the surface in the lumen of the shell, thereafter disposing the core in the lumen in the shell, sealing the core in the shell after the desired positioning of the core in the shell, providing one end of the core with a covering and drawing the core through the lumen in the shell with the covering on the core and removing the covering on the core after the core has been drawn through the lumen in the shell.

* * * * *